United States Patent [19]

Wise

[11] Patent Number: 4,750,829
[45] Date of Patent: Jun. 14, 1988

[54] IRIDOTOMY-SPHINCTEROTOMY CONTACT LENS

[76] Inventor: James B. Wise, 3401 Hickory Stick Rd., Oklahoma City, Okla. 73120

[21] Appl. No.: 861,507

[22] Filed: May 9, 1986

[51] Int. Cl.⁴ .......................... A61B 3/00; G02C 7/04
[52] U.S. Cl. .................................. 351/160 R; 351/219
[58] Field of Search ............... 351/160 R, 160 H, 161, 351/162, 219

[56] References Cited

U.S. PATENT DOCUMENTS

| | | | |
|---|---|---|---|
| 4,391,275 | 7/1983 | Fankhauser et al. | 128/303.1 |
| 4,502,764 | 3/1985 | Riquin | 351/160 R |
| 4,506,962 | 3/1985 | Roussel | 351/160 R |

OTHER PUBLICATIONS

Book entitled, "Ophthalmic Lasers: Current Clinical Uses", edited by Wayne F. March, M.D., pp. 75, 78, 79, 80 and 84.

Primary Examiner—John K. Corbin
Assistant Examiner—Scott J. Sugarman
Attorney, Agent, or Firm—Christensen, O'Connor, Johnson & Kindness

[57] ABSTRACT

A laser iridotomy sphincterotomy contact lens having a high-power (103 diopter) entry lens decentered 2.5 millimeters from the contact lens. Very small iris focal spots and high-energy density are practically achievable.

8 Claims, 1 Drawing Sheet

IRIDOTOMY-SPHINCTEROTOMY CONTACT LENS

BACKGROUND OF THE INVENTION

The present invention relates to contact lenses utilized in ophthalmic surgery and, more particularly, to contact lenses that improve the delivery of laser energy during ophthalmic surgery.

Eye diseases such as glaucoma inhibit the free circulation of aqueous humor within the eyeball. One method of treating diseases such as glaucoma is to perforate eye tissues such as the iris to promote the flow of aqueous humor. Lasers have been effectively employed for iris perforation. When laser iridectomy was initially performed with the millisecond-pulsed and Q-switched ruby lasers and with continuous wave and pulsed argon lasers, the procedure was performed either with no contact lenses or with the plano surface of the Goldmann style contact lens. The Goldmann contact lens has a plano entry surface that is oriented orthogonally to the optical axis of the lens and an exit surface that conforms to the shape of the cornea. When used, the Goldmann contact lens served only to separate the eyelids and to dampen ocular motions. An improvement over the Goldmann lens is the Abraham style iridectomy lens, which converges the laser beam through a 66-diopter button lens placed offcenter on a plano Goldmann carrier lens. The Abraham lens significantly improves the efficacy of laser iridectomy by producing a higher energy density at the iris, while reducing energy density at the cornea and retina. The Abraham iridectomy lens has thus been an important factor in bringing argon laser iridectomy to the status of an accepted standard procedure.

However, even using the Abraham lens, difficulty can occur in perforating very light blue irides, which absorb the laser energy poorly, and thick dark brown irides, which tend to char and shrink. In particular, light blue irides can require high-energy levels that represent a hazard to the macula. The linear incision technique of laser iridotomy and iris sphincterotomy utilize multiple short-duration laser burns to make linear cuts across intrinsic iris tension lines. This method increases the efficiency of iris perforation and produces true iridotomies rather than iridectomies. This method also reduces but does not completely eliminate the difficulties encountered with light blue or thick brown irides.

To avoid the corneal and retinal hazards resulting from high-burn energies, and to further increase the effectiveness of iridotomy and iris sphincterotomy, it would be desirable to selectively increase the energy density at the iris surface above that obtainable with the Abraham iridectomy lens without increasing the actual level of laser energy delivered. Such a selective increase requires additional laser beam convergence to decrease the size of the laser "spot" on the iris. In theory, laser beam convergence is obtainable either by increasing the cone angle of the beam produced by the laser instrument, or by using a strongly converging contact lens. Increasing the cone angle of the laser beam, however, is severely restricted by the constraints of laser design and delivery.

Prior contact lenses with a greater convergence than the Abraham iridectomy lens have, however, met with only limited success. One such lens has its optical center in the center of the carrier ring than offset as in the Abraham iridectomy lens. To bring the optic center over the peripheral iris, either the patient must look down or the lens must be lifted. Downward gaze by a patient is often difficult to maintain under the stimulus of bright laser flashes. On the other hand, lens tilting induces astigmatism and corneal wrinkling. Moreover, the prior lenses are relatively large and markedly reduce the distance between the laser and the lens, thus giving rise to clearance problems between the laser and the lens and between the laser and the nose. It was also thought that increasing the cone angle of a laser beam using a more strongly converging contact lens than the Abraham iridectomy lens would lead to spherical aberrations that would detrimentally affect the desired end result of producing a smaller effective "spot" size at the focal plane of the lens.

SUMMARY OF THE INVENTION

The present invention provides a contact lens that increases the convergence of the laser beam and, at the same time, effectively reducing the iris focal spot size and increasing the energy density obtainable within the focal spot. The increased iris energy density is almost eight times greater than that achieved with a plano contact lens and almost three times greater than that achievable with the Abraham iridectomy lens. Thus, the iris burn temperature level can be increased above the threshold level for evaporative pyrolysis even at very short exposures, thus facilitating argon laser iridotomy and iris sphincterotomy by the linear incision method. Crystalline lens and corneal burns are essentially eliminated by the very shallow focal depth achieved with the lens constructed in accordance with the present invention and with the ability to use less energy per burn because of the reduced iris focal spot achieved with the lens. For example, for a given iris energy density, the lens produced in accordance with the present invention protects the macula by reducing retinal energy density to 1.2% of that produced by plano contact lens and to about 9% of that produced by an Abraham iridectomy lens.

A lens constructed in accordance with the present invention comprises a contact lens having a concave surface with a radius of curvature substantially equivalent to the radius of curvature of the cornea of an eye. The contact lens has a plano surface oriented orthogonally to the optical axis of the contact lens. The contact lens further includes a convex-plano entry lens having a plano exit surface oriented orthogonally to the optical axis of the entry lens. The plano exit surface is mounted contiguously with the plano entry surface of the contact lens, while the optical axis of the entry and contact lenses are offset to facilitate iridotomy and iris sphincterotomies. The entry lens has a power ranging from 93 to 112 diopters. The combined thickness of the entry and contact lenses are sufficient to focus a converging laser beam entering the entry lens on the iris of an eye when the contact lens is in contact with the cornea of the eye. Preferable power of the entry lens is 98 to 108 diopters while a power of 103 diopters is optimum.

BRIEF DESCRIPTION OF THE DRAWINGS

A better understanding of the present invention can be derived by reading the ensuing specification in conjunction with the accompanying drawings wherein.

DETAILED DESCRIPTION

Figure 1:
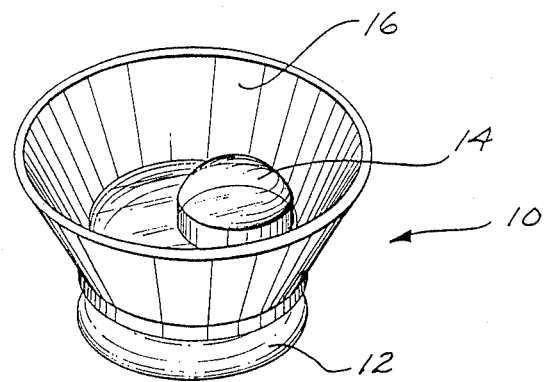
FIG. 1 is an isometric view of a contact lens constructed in accordance with the present invention.

First, referring to FIG. 1, the iridotomy lens 10 constructed in accordance with the present invention includes contact lens 12, an entry or button lens 14, and a lens shade 16. Lens shades conventionally eliminate stray light and unwanted reflections from entering the lenses, which might interfere with use of the lens during surgery.

Figure 2:
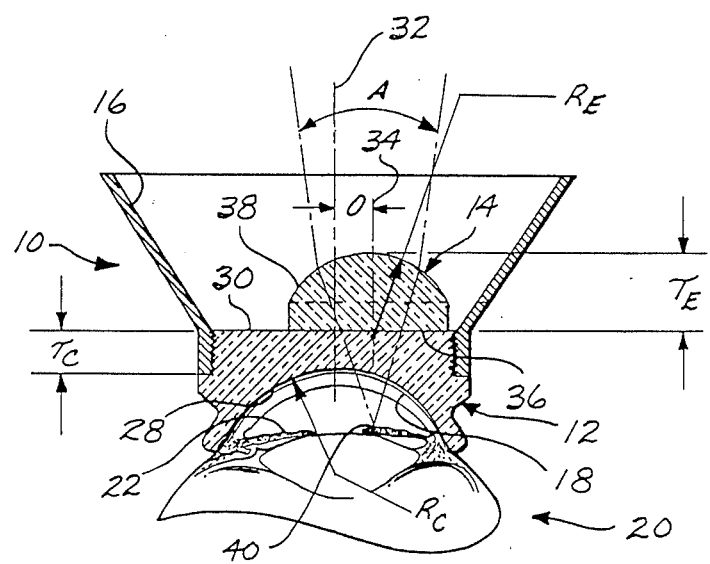
FIG. 2 is a longitudinal section view through the optical axes of the entry and contact lenses comprising the lens constructed in accordance with the present invention.

Referring now to FIG. 2, the iridotomy lens 10 is shown in contact with the cornea 18 of an eye 20. Most of the structure of the rest of the eye has been eliminated for simplicity, leaving only the iris 22 and the crystalline lens depicted in this figure. The contact lens 12 has an exit surface 28 having a radius of curvature $R_C$. The radius $R_C$ corresponds to the average radius of curvature of the cornea 18. The entry surface 30 of the contact lens 12 is planar and is oriented orthogonally to the optical axis 32 of the contact lens 12. The optical axis 34 of the entry lens 14 is offset by distance "O" from the optical axis of the contact lens 12. The exit surface of the entry lens 14 is planar and is orthogonally oriented relative to the optical axis 34. The exit surface 36 of the entry lens and the entrance surface of the contact lens are abutted and are permanently secured to each other by conventional adhesives. The convex entry surface 38 of the entry lens 14 has a radius of curvature $R_E$. The thickness of the contact lens is $T_C$ while the thickness of the entry lens is $T_E$. In its most preferred form, $R_C$ is 7.45 millimeters, $R_E$ is 5.0 millimeters, $T_C$ is 1 millimeter, $T_E$ is 4.0 millimeters, and the offset "O" is 2.5 millimeters. While the foregoing dimensions are preferred, it is understood that slight variations from these dimensions still will yield an operable lens, but one which provides results that are less than the best. For example, the radius of curvature $R_E$ is 5.0 millimeters and provides a power of 103 diopters. It is to be understood that the entry lens is operable with a power ranging from 93 to 112 diopters. Powers greater than 112 diopters are unworkable because the problems produced by spherical aberrations overcome any increase in efficacy provided by increasing the power. Higher powers may also make it difficult to focus on the iris of patients with deep anterior chambers. It is therefore preferable that the power of the lens be in a range of from 98 to 108 diopters and, more preferably, in the range of 101 to 105 diopters and optimally at 103 diopters.

In the illustrated embodiment, the entry lens is produced from a high-grade optical glass while the contact lens is produced from a polymethyl methacrylate polymer. All of the surfaces of both the glass and polymer are coated with antireflective coatings in a conventional manner.

The lens produced in accordance with the present invention is used in a manner similar to prior contact lenses. Multiple laser burns are placed back and forth in horizontal lines across the fibers of the superior peripheral iris or up and down in a vertical line across the iris sphincter at the upper margin of the pupil. Exposure times are on the order of 0.01 seconds for dark brown thick irides, 0.01 to 0.02 seconds for brown and hazel irides, and 0.02 to 0.05 (rarely up to 0.10 seconds) for the stroma of light blue irides. Bridging strands are cut and pigment epithelium are removed at 0.01 or 0.02 seconds only. Energy levels of 300 to 1500 mw and total burn numbers of 85 to 555 are used for iridotomies. Up to 1,934 burns at 0.01 seconds in low-energy levels are used for sphincterotomies. Because so little energy is delivered (and quickly dissipated) per burn, no upper limit is necessarily placed upon the total number of burns. In most conditions, whatever number is required for precisely controlled iris incision of the proper size can be employed while minimizing risk to cornea lens and retina for the careful use of low-energy levels. As always, emphasis should always be upon precision and safety rather than upon speed, even though it is possible to complete large iridotomies in three to four minutes.

When the lens produced in accordance with the present invention is employed with laser beams having convergences (or cone angles A) of 8.5° and 4.5°, the 103 diopter lens provides the theoretically smallest size iris focal spot 40 of any lens tested. Lenses having lesser power can give similar focal spots and cone angles. However, lesser power lenses require thicker lens construction, in turn requiring the laser to be much closer to the eye than it is with the lens produced in accordance with the present invention. Of course, when the laser is positioned closer to the eye, clearance problems again become predominant.

In use with a continuous wave argon blue-green laser with a fiber optic delivery system (for example, of the type available from Coherent, Inc., Model 920), which gives an 8.5° beam convergence angle, the preferred lens produces an effective iris focal spot of approximately 18.84 microns. For a given laser output, the most preferred lens (103 diopters) produces an energy density at the iris surface 7.79 times greater than that produced by prior art plano lenses, and 2.92 times greater than that produced by the prior Abraham iridectomy lenses. In this arrangement, the cone angle of the beam striking the iris is increased from 8.5° to 19.6°. For a given iris energy density, the retinal energy density is reduced by the most preferred lens to a level that is 1.2% of that produced by the prior plano lens and 8.7% of that produced by the Abraham iridectomy lens. The preferred lens therefore markedly reduces the risk of macular injury.

When the preferred lens is used with a continuous wave argon green laser having 4.5° beam cone angle (available from CooperVision, Inc., Model 85,000), an effective iris focal spot size of approximately 10.76 microns can be achieved. This arrangement provides a similar improvement efficiency to that which can be achieved with an 8.5° cone angle laser.

Another advantage obtained with the present invention is that the magnification of the iris image seen by the physician is greater than that achieved with the prior art lenses. Greater magnification allows precise aiming and focusing for maximum utilization of the higher energy density delivery. For example, the 103 diopter lens of the present invention produces a magnification of 2.65× while the prior Abraham iridectomy lens produces a magnification of only 1.55× and while the prior plano contact lenses produce a magnification of 0.95×.

The nearly tripled energy density achieved utilizing the iridotomy lens of the present invention produces a marked change in the response of the iris during laser surgery. For example, as the iris temperature is progressively increased, the iris initially shrinks. It then denatures and darkens, chars and carbonizes, and finally undergoes complete pyrolysis and evaporates. For each level of effect, there is a threshold temperature, although the exact threshold levels have not been quantitatively determined. The very high energy density produced by the lens constructed in accordance with the invention allows the evaporative temperature threshold level for the iris to be achieved at lower output energies or shorter burn durations. Because the evaporative temperature threshold can usually be obtained, the burn duration using the lens of the present invention is very short (0.01 or 0.02 seconds), heat conduction is less, and nearly all the applied laser energy evaporates the iris, rather than being partially wasted in the production of a surrounding zone of charred tissue.

Moreover, the lens produced in accordance with the present invention will allow surgeons to employ lasers that with prior lenses were unable to achieve the threshold temperature for evaporative pyrolysis of the iris. For example, many prior argon lasers produced poorly focused spots with poor energy density. These lasers have therefore not been able to generate an iris temperature level higher than the shrinkage and carbonizing level. However, with the use of a lens produced in accordance with the present invention, production of an adequately high iris temperature level for a successful iridotomy can be achieved.

The present invention has been described in conjunction with preferred embodiments of the invention. One of ordinary skill will readily ascertain that various alterations, substitutions of equivalents and other changes can be made without departing from the concepts herein imparted. Moreover, the lens has been disclosed as especially efficacious in connection with iridotomies and sphincterotomies. One of ordinary skill will quickly realize that the lens has broad applicability for a variety of procedures in the anterior chamber, for example, cutting vitreous bands, cutting sutures, treating cysts, and treating blood vessels in the iris and cornea. In addition, the lens can be employed with lasers other than the standard argon laser, including the argon-green laser, the Krypton laser, the Yag lasers, and the tuneable dye laser. It is therefore intended that Letters Patent granted herein shall be limited only by the definition contained in the appended claims and equivalents thereof.

The embodiments of the invention in which an exclusive property or privilege is claimed are defined as follows:

1. A lens for use in ophthalmic surgery comprising:
   a contact lens having a concave exit surface, said concave exit surface having a radius of curvature substantially equivalent to the radius of curvature of the cornea of an eye, said contact lens having a plano entrance surface oriented orthogonally to the optical axis of the contact lens; and
   a convex-plano entry lens having a plano exit surface oriented orthogonally to the optical axis of said entry lens, said plano exit surface being mounted contiguously on the plano entry surface of said contact lens, the optical axis of said entry and said contact lenes being offset, said entry lens having a power ranging from 93 to 112 diopters, the combined thickness of said entry lens and said contact lens being sufficient to focus a converging laser beam entering said entry lens on the iris of an eye when said contact lens is in contact with the cornea of said eye, both of said lens being transparent to visible light.

2. The lens of claim 1, wherein said entry lens has a power in the range of from 98 to 108 diopters.

3. The lens of claim 2, wherein said entry lens has a power in the range of 101 to 105 diopters.

4. The lens of claim 3, wherein said entry lens has a power of 103 diopters.

5. The lens of claim 1, wherein the radius of curvature of the entry surface of said entry lens is about 5.0 millimeters.

6. The lens of claim 5, wherein the combined thickness of said entry lens and said contact lens along their respective optical axis is 5 millimeters.

7. The lens of claim 6, wherein said optical axis of said entry lens and said contact lens are offset by 2.5 millimeters plus or minus 0.1 millimeter.

8. The lens of claim 7, wherein said entry surface of said contact lens has a radius of curvature of approximately 7.45 millimeters.

* * * * *